US006284894B1

(12) United States Patent
Ek et al.

(10) Patent No.: US 6,284,894 B1
(45) Date of Patent: Sep. 4, 2001

(54) PREPARATION OF ALLYLIC AROMATIC COMPOUNDS

(75) Inventors: Fredrik Ek, Lund; Lars Goran Wistrand, Malmo, both of (SE)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/466,222

(22) Filed: Dec. 17, 1999

Related U.S. Application Data
(60) Provisional application No. 60/116,981, filed on Jan. 25, 1999.

(30) Foreign Application Priority Data

Dec. 18, 1998 (GB) .................................................. 9828103

(51) Int. Cl.$^7$ ......................... C07C 205/06; C07C 17/26; C07C 25/24; C07C 25/28
(52) U.S. Cl. .......................... 546/304; 560/20; 560/254; 562/437; 564/305; 568/306; 568/584; 568/932; 568/933; 568/936; 568/937; 568/939; 568/940; 570/182; 570/200
(58) Field of Search ............................... 546/304; 560/20, 560/254; 562/437; 564/305; 568/306, 584, 932, 933, 936, 937, 939, 940; 570/182, 200

(56) References Cited

U.S. PATENT DOCUMENTS 5,475,176 * 12/1995 Beller et al. .......................... 585/438

OTHER PUBLICATIONS

Jacek Porwisiak and Manfred Schlosser, "1–Bromo–3, 5–bis(trifluoromethyl)benzene: A Versatile Starting Material for Organometallic Synthesis", Chem. Ber, 1996, XP002133846.
Migita, T. et al., "$S_H{}'$ Type Reactions of Substituted Allylic Compounds", Tetrahedron, 1973.
Kiyoshige Takayama et al., "Reactivities of Aryl Radicals in Hydrogen Abstraction and Addition", Chemistry Letters, 1973.
Migita, T. et al., "Relative Reactivities of Substituted Phenyl Radicals in Elementary Reactions", 1979, J.C.S. Perkin II.
Migita, T. et al., Free Radical Chain Reaction of Allylic Tin Compounds with Organic Halides Involving $S_H{}'$ Process, 1983, The Chemical Society of Japan.
Al Adel, I. et al., Bulletin de la Societe Chimique de France partie II–Chimie Moleculaire Organique et biologique, 1976, 5–6, 934–938.
M.P. Doyle et al., "Alkyl Nitrite–Metal Halide Deamination Reactions. 3. Arylation of Olefinic Compounds in the Deamination of Arylamines by Alkyl Nitrites and Copper (II) Halides. A Convenient and Effective Variation of the Meerwein Arylation Reaction", 1977, J. Org. Chem.

* cited by examiner

*Primary Examiner*—Samuel Barts
*Assistant Examiner*—Brian J. Davis
(74) *Attorney, Agent, or Firm*—Bacon & Thomas

(57) ABSTRACT

A process for the preparation of an allylic aromatic compound in which an aromatic amine is reacted first with a nitrite and then with an allylic olefin having an eliminatable terminal substituent. Novel allylic derivatives of disubstituted benzene compounds are also described.

6 Claims, No Drawings

PREPARATION OF ALLYLIC AROMATIC COMPOUNDS

This application claims benefit under 35 U.S.C. 119(e) of application 60/116,981, filed Jan. 15, 1999.

This invention is concerned with the preparation of allylic aromatic compounds.

A number of methods are known for the introduction of an allylic group into an aromatic compound, such as cross-coupling or direct allylation, but these often require the use of expensive and toxic metal reagents or catalysts, e.g. Sn or Pd, or air (oxygen) and water sensitive reagents and substrates which are difficult to work with on a large scale. It has often been shown that aromatic compounds substituted with electron withdrawing groups produce allylated products after extended reaction times and in reduced yield. Allylation of an aromatic carbon via a radical intermediate (e.g. a phenyl radical) has also been proposed (e.g. Migita et al., Bull. Chem. Soc. Jpn, 56, 2480–2484 (1983)), but these reactions require either at least two process steps and unstable and toxic intermediates or the use of toxic tin catalysts.

These methods are therefore unsuitable for use on a large scale, particularly in the manufacture of compounds required as intermediates for use in the production of medical products. An important example of an allylic compound of this kind is allyl-3,5-dinitrobenzene, which can be used in the production of iodinated X-ray contrast agents containing dihydroxypropyl side chains, such as described in WO 96/09282.

We have now found a new method of preparing allylic aromatic compounds such as allyl-3,5-dinitrobenzene which can give the required product in high yield from commercially available and less hazardous starting materials without the use of metal reagents or catalysts. The procedure is more convenient in that only a single process step is required and the reaction time is short. The method is therefore suitable for use for large scale manufacture.

The invention thus provides a process for the preparation of an allylic aromatic compound in which an aromatic amine is reacted first with a nitrite and then with an allylic olefin having an eliminatable terminal substituent.

The aromatic amine starting material may for example be substituted by one or more (and preferably two) electron withdrawing groups and may have the formula R—NH$_2$ where:

R is a phenyl or heterocyclic aromatic group optionally substituted by one or more of the following groups: OH, OX, OCN, OCOX, OCONH$_2$, OSO$_2$H, OSO$_2$X, OSiX$_3$, OPOX$^2$, X, CHO, COX, COOH, COOX, CONHZ, CONX$^2$, CN, NO$_2$, NCO, NCS, NC, NHZ, NX$^2$, NZOH, NZCHO, NZCOX, NZCO$_2$X, NZCONH$_2$, NZSO$_2$X, SH, SX, SOX, SO$_2$X, SO$_2$NHZ, SO$_2$NX$^2$, SCN, F, Cl, Br, B(OH)$_2$, B(OX)$_2$, or PO(OX)$_2$;

X is a phenyl or C$_1$–C$_{10}$ alkyl group optionally substituted by F, Cl, Br and/or substituents containing F, Cl, Br, O, S or N (such as halo-C$_{1-3}$ alkyl, C$_{2-6}$ alkanoyloxy, C$_{1-6}$ alkoxy, OH, OCN, OCONH$_2$, OSO$_2$H, CHO, COOH, CONH$_2$, NC, NO$_2$, NCO, NCS, CN, NH$_2$, SH, SO$_2$NH$_2$ or SCN);

X$^2$ represents two X groups or a C$_{3-8}$ cycloalkyl group optionally substituted as defined for X, for example, F, Cl and/or Br; and Z is H or X.

When R is a heterocyclic group, it may contain O, N or S as the heteroatom and may be monocyclic or bicyclic.

The aromatic amine preferably has the formula (1)

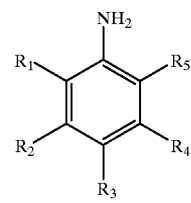

where:

R$_1$, R$_3$ and R$_5$ are independently H or NO$_2$, and R$_2$ and R$_4$ are independently H, NO$_2$, COOH, COOMe, COOEt, CONH$_2$, CONX$^2$, COMe, CN or CF$_3$, provided that at least one (and preferably at least two) of R$_1$–R$_5$ is other than H.

Examples of suitable amines are 3-nitroaniline, 4-nitroaniline, 2,4-dinitroaniline, 2,6-dinitroaniline, 3,5-dinitroaniline, 3-acetyl-5-nitroaniline, 3,5-diacetylaniline, 3-carboxymethyl-5-nitroaniline, 3-carboxyethyl-5,-nitroaniline, 3,5-dicarboxyethylaniline, 3,5-dicarboxymethylaniline and 3,5-bisaminocarbonylaniline.

A preferred amine starting material is 3,5-dinitroaniline.

The nitrite used may be an organic nitrite such as a C$_{1-6}$ alkyl nitrite, preferably t-butylnitrite, or an aromatic nitrite.

The allylic olefin reagent may be a compound of the formula R$^a$L where R$^a$ is a 2,3-alkenyl group (such as a C$_{3-6}$ alkenyl or C$_{5-7}$ cycloalkenyl group which may be optionally substituted) and L is an eliminatable substituent.

The allylic reagent may for example have the formula (2)

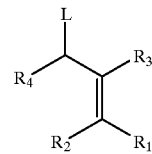

where L is Br, I, SR$^b$, SnR$^b_3$, SiR$^b_3$, Si(TRS)$_3$, SSi(TRS)$_3$, SSnR$^b_3$, SO$_2$R$^b$, SO$_2$CF$_3$, SePh or OPO(OPh)$_2$ (where TRS is trialkylsilyl and R$^b$ is C$_{1-6}$ alkyl, C$_{2-6}$ alkenyl or aryl such as phenyl or tolyl), and R$_1$–R$_4$, independently, is each a hydrogen atom or a phenyl or C$_1$–C$_{10}$ alkyl group optionally substituted by F, Cl, Br and/or substituents containing F, Cl, Br, O, S, N such as given above for X. R$^1$ and R$^3$ may also be Br or —COOH Examples of such compounds are 3-bromopropene, 3-bromo-2-methylpropene, 2-bromomethylacrylic acid, 2-acetoxymethyl-3-bromopropene, 1,4-dibromo-2-butene, 1-acetoxy-4-bromo-2-butene, 1-hydroxy-2-bromo-3-butene, 1-acetoxy-2-bromo-3-butene, allyldisulfide, allylsulfide, allylmethylsulfide, allyliodide and allyl bromide.

It is believed that in the initial stage of the reaction, the nitrite diazotises the aromatic amine and forms an aryl radical which then reacts with the allylic reagent R$^a$L to produce the required allylic aromatic compound by elimination of the substituent L.

In reactions where the allylic reagent and/or the nitrite are liquid it is not necessary to use a solvent, but a polar solvent such as acetonitrile or dimethyl-sulphoxide can be used if required. The reaction temperature is preferably kept relatively low (e.g. 5–15° C.), and if desired can then be increased to 20–40° C., conveniently room temperature, to ensure that the reaction is completed.

As indicated above, the process of the invention is particularly suitable for the preparation of 1-allyl-3,5- dinitrobenzene, which is a new compound and is a further aspect of the invention. The preparation is preferably conducted by reaction of 3,5-dinitroaniline with t-butylnitrite and allyl bromide, using the allyl bromide and the nitrite as the reaction solvent. The reaction can be completed within 2–2.5 hours to give a yield of over 90% of the required compound, and is suitable for large scale use. This compares very favourably with the use of toxic and expensive tin catalysts. Thus, direct allylation of 3,5-dinitroiodobenzene with tributylallyltin in the presence of a palladium complex catalyst only gave a yield of 20% after a reaction time of one week.

The following examples illustrate the invention.

EXAMPLE 1

1-Allyl-3,5-dinitrobenzene

To a solution of t-butylnitrite (84.6 ml, 0.71 mol) and allylbromide (530 ml, 6.15 mol) in 25 ml $CH_3CN$, 3,5-dinitroaniline (75 g, 0.41 mol) was added spoonwise, so that the temperature was maintained between 11 and 15° C. During the addition of the final ½ of 3,5-dinitroaniline, more t-butylnitrite (21 ml, 0.18 mol) was added. The reaction mixture was then stirred at room temperature for 1 h. Excess t-butylnitrite, allylbromide and $CH_3CN$ was distilled from the reaction mixture at reduced pressure and the residue was dissolved in toluene (500 ml). The solution was filtered through two $Al_2O_3$ pads. The toluene was distilled off at reduced pressure and to the remaining residue 3,3,5-trimethylpentane (200 ml) was added. The mixture was heated to 60° C. and stirred for ½ h and then cooled to −60° C. The pentane phase was decanted and the mixture was crystallized from 2,2,4-trimethylpentane at −50° C. The crystals were then triturated twice with 2,2,4-trimethylpentane at −50° C. The remaining pentane was then removed at reduced pressure, to give 78.7 g (93%) of 3,5-dinitroallylbenzene as yellow oil containing approximately 4% of 3,5-dinitrobromo benzene.

$^1$H-NMR ($CDCl_3$, 300 MHz) δ ppm: 8.90 (t, J=2.0 Hz, 1H), 8.39 (d, J=2.0 Hz, 2H), 6.04–5.90 (m, 1H), 5.30–5.18 (m, 2H), 3.62 (d, J=6.7, 2H). $^{13}$C-NMR ($CDCl_3$, 75.43 MHz) δ ppm: 148.5, 144.5, 133.9, 128.8, 119.1, 116.8, 39.4.

EXAMPLE 2

3-Acetyl-5-nitroallylbenzene

To a solution of t-butylnitrite (0.24 ml, 2.1 mmol) and allylbromide (1.8 ml, 25.2 mmol) in 3 ml $CH_3CN$ 3-acetyl-5-nitroaniline (0.25 g, 1.4 mmol) was added, so that the temperature was maintained between 20 and 25° C., and the mixture was stirred for 10 min at room temperature. The volatile material in the reaction solution was then removed at reduced pressure to give 3-acetyl-5-nitroallylbenzene. $^1$H-NMR ($CDCl_3$, 300 MHz) δ ppm: 8.61 (s, 1H), 8.25 (s, 1H), 8.10 (s, 1H), 6.03–5.88 (m, 1H), 5.23–5.11 (m, 2H), 3.55 (d, 2H).

EXAMPLE 3

1-(2-Methyl-2-propen-1-yl)-3,5-dinitrobenzene

To a solution of t-butylnitrite (0.13 ml, 1.1 mmol) and 3-bromo-2-methylpropene (0.82 ml, 8.25 mmol) in 1 ml $CH_3CN$, 3,5-dinitroaniline (0.10 g, 0.55 mmol) was added at room temperature. The solution was stirred for 17 h at room temperature and then isopropylether was added. The suspension was filtered through a pad of $Al_2O_3$. The volatile material in the solution was removed at reduced pressure to give the title compound. $^1$H-NMR ($CDCl_3$, 300 MHz) δ ppm: 8.92 (t, J=2.1 Hz, 1H), 8.40 (d, J=2.1 Hz, 2H), 5.00 (s, 1H), 4.82 (s, 1H), 3.55 (s, 2H), 1.72 (s, 3H). $^{13}$C-NMR ($CDCl_3$, 75.43 MHz) δ ppm: 148.4, 144.2, 142.0, 129.0, 116.9, 114.8, 43.9, 22.0.

EXAMPLE 4

1-(2-Acetoxymethyl-2-propen-1-yl)-3,5-dinitrobenzene

To a solution of t-butylnitrite (0.47 ml, 4.0 mmol) and 2-acetoxymethyl-3-bromopropene (1.93 g, 10.0 mmol) in 1 ml $CH_3CN$, 3,5-dinitroaniline (0.37 g, 2.0 mmol) was added, while maintaining the temperature between 18 and 24° C. The mixture was stirred for 1 h at room temperature. The volatile material in the solution was removed at reduced pressure. Flash chromatography (heptane/ethylacetate) gave 0.42 g 1-(2-acetoxymethyl-2-propenyl)-3,5-dinitrobenzene. $^1$H-NMR ($CDCl_3$, 300 MHz) δ ppm: 8.94 (t, J=2.1 Hz, 1H), 8.42 (d, J=2.1 Hz, 2H), 5.33 (s, 1H), 5.05 (s, 1H), 4.52 (s, 2H), 3.64 (s, 2H), 2.08 (s, 3H). $^{13}$C-NMR ($CDCl_3$, 75.43 MHz) δ ppm: 170.4, 148.5, 143.1, 140.7, 129.1, 117.5, 117.2, 65.9, 39.3, 20.7.

EXAMPLE 5

Different Leaving Groups (L)

To a solution of t-butylnitrite (119 μl, 1.0 mmol) and the allylic reagent ($CH_2$=$CHCH_2$L, 5 mmol) in $CH_3CN$ (0.5 ml), 3,5-dinitroaniline (92 mg, 0.5 mmol) was added during 10 minutes, while maintaining the temperature of the reaction mixture at 12–14° C. The reaction mixture was then stirred at 22° C. for one hour. 2-Nitrobenzylalcohol (50 mg) was added as an internal standard. The yield was determined by HPLC.

| L | Yield (%) |
|---|---|
| Br | 74 |
| $SO_2Ph$ | 51 |
| SMe | 28 |
| S(allyl) | 34 |
| SPh | 61 |
| $SiMe_3$ | 25 |
| I | 18 |

EXAMPLE 6

Allyl-2,4-dinitrobenzene

To a solution of t-butylnitrite (119 μl, 1.0 mmol) and allyl bromide (0.65 ml, 7.5 mmol) in $CH_3CN$ (5 ml), 2,4-dinitroaniline (92 mg, 0.5 mmol) was added during 10 minutes, while maintaining the temperature of the reaction mixture at 30–35° C. Extra t-butylnitrite (119 μl, 1.0 mmol) was added to the reaction mixture which then was stirred at 35° C. for one hour. Despite larger amounts of t-butylnitrite and higher reaction temperature, approximately 10% of the aniline was still left accordingly to HPLC. The volatile material in the reaction mixture was then removed at reduced pressure. Chromatography (heptane-ethyl acetate 23:2) gave 60 mg of a 87:13 mixture of allyl-2,4-dinitrobenzene and 2,4-dinitrobromobenzene as a yellow oil, which corresponds to 49% yield of allyl-2,4-dinitrobenzene. $^1$H NMR ($CDCl_3$, 400 MHz) δ 8.77, (d, 1H, J=2.4 Hz), 8.39, (dd, 1H, J=8.5, 2.1 Hz), 7.64, (d, 1H, J=8.5 Hz), 6.01–5.90, (m, 1H), 5.24–5.12, (m, 2H), 3.80, (d, 2H, J=6.5 Hz).

EXAMPLE 7

Allyl-2-cyano-4-nitrobenzene

To a solution of t-butylnitrite (535 μl, 4.5 mmol) and allyl bromide (3.9 ml, 45.0 mmol) in $CH_3CN$ (3 ml), 2-cyano-4-nitroaniline (489 mg, 3.0 mmol) was added during 40 minutes, while maintaining the temperature of the reaction mixture at 23–27° C. At the end of the addition of the aniline, extra t-butylnitrite (180 μl, 1.5 mmol) was added to the reaction mixture which then was stirred at 26° C. for one hour. The volatile material in the reaction mixture was removed at reduced pressure. Column chromatography (heptane-ethyl acetate 23:2) gave 367 mg (65%) of allyl-2-cyano-4-nitrobenzene as an orange oil. $^1$H NMR ($CDCl_3$, 400 MHz) δ 8.51, (d, 1H, J=2.4 Hz), 8.39, (dd, 1H, J=8.6, 2.4 Hz), 7.58, (dd, 1H, J=8.6, 0.5 Hz), 6.00–5.90, (m, 1H), 5.29–5.17, (m, 2H), 3.74, (d, 2H, J=6.6 Hz); $^{13}$C NMR ($CDCl_3$, 100 MHz) δ 151.3, 146.8, 133.5, 131.4, 128.4, 127.9, 119.6, 116.2, 114.4, 38.9; Anal HRMS Calcd. for $C_{10}H_8N_2O_2$ (M): 188.0585.
Found: 188.0585.

EXAMPLE 8

Allyl-4-nitro-2-trifluoromethylbenzene

To a solution of t-butylnitrite (535 μl, 4.5 mmol) and allyl bromide (3.9 ml, 45.0 mmol) in $CH_3CN$ (3 ml), 4-nitro-2-trifluoromethylaniline (618 mg, 3.0 mmol) was added during 20 minutes while maintaining the temperature of the reaction mixture at 18–19° C. At the end of the addition of the aniline, extra t-butylnitrite (180 μl, 1.5 mmol) was added to the reaction mixture which then was stirred at 25° C. for one hour. The volatile material in the reaction mixture was removed at reduced pressure. Column chromatography (heptane-ethyl acetate 49:1) gave 587 mg (85%) of allyl-4-nitro-2-trifluoromethylbenzene as a light yellow oil. $^1$H NMR ($CDCl_3$, 400 MHz) δ 8.53, (d, 1H, J=2.4 Hz), 8.35, (dd, 1H, J=8.5, 2.4 Hz), 7.59, (d, 1H, J=8.5 Hz), 6.00–5.88, (m, 1H), 5.24–5.12, (m, 2H), 3.68, (d, 2H, J=6.5 Hz); $^{13}$C NMR ($CDCl_3$, 100 MHz) δ 146.8, 146.6, 134.9, 133.0, 130.3, (q, J=32.2 Hz), 127.7, 126.9, 124.9, 122.2, 122.1, (q, J=6.0 Hz), 118.7, 37.0, (m); Anal HRMS Calcd. for $C_{10}H_8F_3NO_2$ (M): 231.0507. Found: 208.0515.

EXAMPLE 9

Allyl-4-nitro-3-trifluoromethylbenzene

To a solution of t-butylnitrite (535 μl, 4.5 mmol) and allyl bromide (3.9 ml, 45.0 mmol) in $CH_3CN$ (3 ml), 4-nitro-3-trifluoromethylaniline (618 mg, 3.0 mmol) was added during 20 minutes, while maintaining the temperature of the reaction mixture between 13–15° C. At the end of the addition of the aniline, extra t-butylnitrite (180 μl, 1.5 mmol) was added to the reaction mixture which then was stirred at 25° C. for one hour. The volatile material in the reaction mixture was removed at reduced pressure. Column chromatography (heptane-ethyl acetate 97:3) gave 430 mg (62%) of allyl-4-nitro-3-trifluoromethylbenzene as a light yellow oil. $^1$H NMR ($CDCl_3$, 400 MHz) δ 7.86, (d, 1H, J=8.3 Hz), 7.65, (d, 1H, J=1.2 Hz), 7.55, (dd, 1H, J=8.3, 1.4 Hz), 6.00–5.89, (m, 1H), 5.26–5.14, (m, 2H), 3.54, (d, 2H, J=6.7 Hz); $^{13}$C NMR ($CDCl_3$, 100 MHz) δ 146.5, 135.0, 133.3, 128.5, (q, J=5.0 Hz), 125.8, 124.4, 124.1, 123.8, 121.1, 118.8, 40.0; Anal HRMS Calcd. for $C_{10}H_8F_3NO_2$ (M): 231.0507. Found: 208.0499.

EXAMPLE 10

2-Allyl-5-nitrobenzophenone

To a solution of t-butylnitrite (535 μl, 4.5 mmol) and allyl bromide (3.9 ml, 45.0 mmol) in $CH_3CN$ (3 ml), 2-amino-5-nitrobenzophenone (727 mg, 3.0 mmol) was added during 20 minutes while maintaining the temperature of the reaction mixture at 28–32° C. At the end of the addition of the aniline, extra t-butylnitrite (360 μl, 3 mmol) was added to the reaction mixture which then was stirred at 25° C. for one hour. The volatile material in the reaction mixture was removed at reduced pressure. Column chromatography (heptane-ethyl acetate 23:2) gave 370 mg (46%) of 2-allyl-5-nitrobenzophenone as a light yellow oil. $^1$H NMR ($CDCl_3$, 300 MHz) δ 8.29, (dd, 1H, J=8.6, 2.5 Hz), 8.18, (d, 1H, J=2.4 Hz), 7.81–7.74, (m, 2H), 7.69–7.60, (m, 1H), 7.57–7.45, (m, 3H), 5.93–5.88, (m, 1H), 5.09–5.95, (m, 2H), 3.53, (m, 2H, J=6.6 Hz).

EXAMPLE 11

Ethyl 3-allyl-5-nitrobenzoate

To a solution of t-butylnitrite (535 μl, 4.5 mmol) and allyl bromide (3.9 ml, 45.0 mmol) in $CH_3CN$ (3 ml), ethyl 3-amino-5-nitrobenzoate (631 mg, 3.0 mmol) was added during 20 minutes while maintaining the temperature of the reaction mixture at 10–12° C. At the end of the addition of the aniline, extra t-butylnitrite (180 μl, 1.5 mmol) was added to the reaction mixture which then was stirred at 25° C. for one hour. The volatile material in the reaction mixture was removed at reduced pressure. Column chromatography (heptane-ethyl acetate 47:3) gave 470 mg (67%) of ethyl 3-allyl-5-nitrobenzoate as a light yellow oil, which crystallized upon standing overnight in the refrigerator. $^1$H NMR ($CDCl_3$, 400 MHz) δ 8.70, (m, 1H), 8.24, (m, 1H), 8.20, (m, 1H), 6.03–5.91, (m, 1H), 5.24–5.13, (m, 2H), 4.44, (q, 2H, J=7.1 Hz), 3.56, (d, 2H, J=6.5 Hz), 1.44, (t, 3H, J=7.1 Hz); $^{13}$C NMR ($CDCl_3$, 100 MHz) δ 165.0, 148.8, 143.1, 135.9, 135.5, 132.6, 127.7, 122.9, 118.4, 62.3, 39.9, 14.7; Anal HRMS Calcd. for $C_{12}H_{13}NO_4$ (M): 235.0845. Found: 235.0846.

EXAMPLE 12

Allyl-2-chloro-4-nitrobenzene

To a solution of t-butylnitrite (535 μl, 4.5 mmol) and allyl bromide (3.9 ml, 45.0 mmol) in $CH_3CN$ (3 ml), 2-chloro-4-nitroaniline (518 mg, 3.0 mmol) was added during 20 minutes, while maintaining the temperature of the reaction mixture at 11–13° C. At the end of the addition of the aniline, extra t-butylnitrite (180 μl, 1.5 mmol) was added to the reaction mixture which then was stirred at 23° C. for one hour. The volatile material in the reaction mixture was then removed at reduced pressure. Column chromatography (heptane-ethyl acetate 97:3) gave 497 mg (84%) allyl-2-chloro-4-nitrobenzene as a light yellow oil containing 5% of 2-chloro-4-nitrobromobenzene. This corresponds to 79% yield of allyl-2-chloro-4-nitrobenzene. $^1$H NMR ($CDCl_3$, 400 MHz) δ 8.25, (d, 1H, J=2.4 Hz), 8.08, (dd, 1H, J=8.5, 2.3 Hz), 7.42, (d, 1H, J=8.5 Hz), 6.01–5.89, (m, 1H), 5.23–5.10, (m, 2H), 3.59, (d, 2H, J=6.5 Hz); $^{13}$C NMR ($CDCl_3$, 100 MHz) δ 147.3, 145.9, 135.3, 134.0, 131.2, 125.0, 122.2, 118.5, 38.0; Anal HRMS Calcd. for $C_9H_8ClNO_2$ (M): 197.0244. Found: 197.0247.

EXAMPLE 13

Allyl-2-bromo-5-nitrobenzene

To a solution of t-butylnitrite (535 µl, 4.5 mmol) and allyl bromide (3.9 ml, 45.0 mmol) in $CH_3CN$ (3 ml), 2-bromo-5-nitroaniline (651 mg, 3.0 mmol) was added during 20 minutes, while maintaining the temperature of the reaction mixture at 35–40° C. At the end of the addition of the aniline, extra t-butylnitrite (180 µl, 1.5 mmol) was added to the reaction mixture which then was stirred at 23° C. for one hour. The volatile material in the reaction mixture was removed at reduced pressure. Column chromatography (heptane-ethyl acetate 49:1) gave 568 mg (78%) allyl-2-bromo-5-nitrobenzene as a light yellow oil containing 7% of 3,4-dibromo-nitrobenzene, which crystallized upon standing overnight in the refrigerator. This corresponds to 72% yield of allyl-2-bromo-5-nitrobenzene. The allyl-2-bromo-5-nitrobenzene could be purified by crystallization from pentane. $^1$H NMR ($CDCl_3$, 400 MHz) δ 8.10, (d, 1H, J=2.7 Hz), 7.95, (dd, 1H, J=8.7, 2.7 Hz), 7.74, (d, 1H, J=8.7 Hz), 6.03–5.92, (m, 1H), 5.26–5.13, (m, 2H), 3.60, (m, 2H, J=6.5 Hz); $^{13}$C NMR ($CDCl_3$, 100 MHz) δ 147.7, 142.0, 134.1, 134.1, 132.3, 125.3, 122.9, 118.8, 40.5; Anal HRMS Calcd. for $C_9H_8BrNO_2$ (M): 240.9738. Found: 240.9739.

EXAMPLE 14

Allyl-4-methoxy-3-nitrobenzene

To a solution of t-butylnitrite (535 µl, 4.5 mmol) and allyl bromide (3.9 ml, 45.0 mmol) in $CH_3CN$ (3 ml), 4-methoxy-3-nitroaniline (504 mg, 3.0 mmol) was added during 20 minutes, while maintaining the temperature of the reaction mixture at 35–40° C. At the end of the addition of the aniline, extra t-butylnitrite (180 µl, 1.5 mmol) was added to the reaction mixture which then was stirred at 40° C. for one hour. The volatile material in the reaction mixture was removed at reduced pressure. The crude product was dissolved in ethyl acetate-heptane (1:2, 20 ml) and filtered through a pad of silica. The solvent was removed at reduced pressure. Column chromatography (heptane-ethyl acetate 97:3) gave 230 mg (40%) allyl-4-methoxy-3-nitrobenzene as a yellow oil. $^1$H NMR ($CDCl_3$, 400 MHz) δ 7.45, (d, 1H, J=2.7 Hz), 7.27, (d, 1H, J=8.6 Hz), 7.10, (dd, 1H, J=8.6, 2.7 Hz), 6.02–5.90, (m, 1H), 5.12–5.02, (m, 2H), 3.86, (s, 3H), 3.62, (m, 2H, J=6.4 Hz); $^{13}$C NMR ($CDCl_3$, 100 MHz) δ 158.8, 150.0, 135.9, 133.2, 127.2, 120.2, 117.1, 109.6, 56.2, 36.8; Anal HRMS Calcd. for $C_{10}H_{11}NO_3$ (M): 193.0739. Found: 193.0743

EXAMPLE 15

Allyl-2-methyl-3-nitrobenzene

To a solution of t-butylnitrite (535 µl, 4.5 mmol) and allyl bromide (3.9 ml, 45.0 mmol) in $CH_3CN$ (3 ml), 2-methyl-3-nitroaniline (651 mg, 3.0 mmol) was added during 20 minutes, while maintaining the temperature of the reaction mixture at 32–35° C. At the end of the addition of the aniline, extra t-butylnitrite (180 µl, 1.5 mmol) was added to the reaction mixture which then was stirred at 23° C. for one hour. The volatile material in the reaction mixture was removed at reduced pressure. Column chromatography (heptane-ethyl acetate 49:1) gave 370 mg of a 25:6:69 mixture of 2-methyl-3-nitrobromobenzene, monobromo-1-allyl-2-methyl-3-nitrobenzene and of allyl-2-methyl-3-nitrobenzene. (The byproducts have been identified with HRMS). This corresponds to 43% yield of allyl-2-methyl-3-nitrobenzene. $^1$H NMR ($CDCl_3$, 300 MHz) δ 7.63, (d, 1H, J=8.2 Hz), 7.38, (d, 1H, J=7.4 Hz), 7.26, (t, 1H, J=7.8 Hz), 6.01–5.86, (m, 1H), 5.17–4.93, (m, 2H), 3.47, (m, 2H, J=6.0 Hz), 2.39, (s, 3H); Anal HRMS Calcd. for $C_{10}H_{11}NO_2$ (M): 177.0790. Found: 177.0790.

EXAMPLE 16

Allyl-3,5-dichlorobenzene

To a solution of t-butylnitrite (535 µl, 4.5 mmol) and allyl bromide (3.9 ml, 45.0 mmol) in $CH_3CN$ (3 ml), 3,5-dichloroaniline (486 mg, 3.0 mmol) was added during 20 minutes, while maintaining the temperature of the reaction mixture at 30–35° C. At the end of the addition of the aniline, extra t-butylnitrite (180 µl, 1.5 mmol) was added to the reaction mixture which then was stirred at 23° C. for one hour. The volatile material in the reaction mixture was removed at reduced pressure. Column chromatography (pentane) gave 374 mg of a 17:4:79 mixture of allyl-4-bromo-3,5-dichlorobenzene, bromo-3,5-dichlorobenzene and of allyl-3,5-dichlorobenzene. (The by-products have been identified with HRMS and $^1$H NMR). This corresponds to 48% yield of allyl-3,5-dichlorobenzene. $^1$H NMR ($CDCl_3$, 400 MHz) δ 7.22, (m, 1H, J=1.9, 0.3 Hz), 7.09, (m, 2H, J=1.9 Hz), 5.97–5.86, (m, 1H), 5.18–5.09, (m, 2H), 3.35, (d, 2H, J=6.7 Hz); $^{13}$C NMR ($CDCl_3$, 100 MHz) δ 143.8, 136.1, 135.2, 127.6, 126.8, 117.7, 39.9; Anal HRMS Calcd. for $C_9H_8Cl_2$ (M) 186.0003. Found: 186.0003.

EXAMPLE 17

Allyl-3,5-dibromobenzene

To a solution of t-butylnitrite (59.5 µl, 0.5 mmol) and allyl bromide (0.33 ml, 3.75 mmol) in $CH_3CN$ (0.25 ml), 3,5-dibromoaniline (63 mg, 0.25 mmol) was added during 5 minutes, while maintaining the temperature at 30–350C. The reaction mixture was then stirred at 23° C. for one hour. The volatile material in the reaction mixture was removed at reduced pressure. Column chromatography (pentane) gave 40 mg of a 12:15:73 mixture of allyl-4-bromo-3,5-dibromobenzene, 1,3,5-tribromobenzene and allyl-3,5-dibromobenzene. (The byproducts have been identified with HRMS and $^1$H NMR). This corresponds to 39% yield of allyl-3,5-dibromobenzene. $^1$H NMR ($CDCl_3$, 300 MHz) δ 7.51, (m, 1H, J=1.8, 0.4 Hz), 7.27, (m, 2H, J=1.8 Hz), 5.96–5.82, (m, 1H), 5.17–5.07, (m, 2H), 3.33, (d, 2H, J=6.5 Hz); Anal HRMS Calcd. for $C_9H_8Br_2$ (M): 273.8993. Found: 273.8984.

EXAMPLE 18

4-Allylbromobenzene

To a solution of t-butylnitrite (535 µl, 4.5 mmol) and allyl bromide (3.9 ml, 45.0 mmol) in $CH_3CN$ (3 ml), 4-bromoaniline (516 mg, 3.0 mmol) was added during 20 minutes, while maintaining the temperature of the reaction mixture at 30–35° C. At the end of the addition of the aniline, extra t-butylnitrite (180 µl, 1.5 mmol) was added to the reaction mixture which then was stirred at 30° C. for one hour. The volatile material in the reaction mixture was removed at reduced pressure. Column chromatography (pentane) gave 200 mg (34%) of 4-allylbromobenzene as a clear oil. $^1$H NMR ($CDCl_3$, 400 MHz) δ 7.43, (m, 2H, J=8.3

Hz), 7.08, (m, 2H, J=8.3 Hz), 6.00–5.89, (m, 1H), 5.12–5.05, (m, 2H), 3.35, (d, 2H, J 6.7 Hz); $^{13}$C NMR (CDCl$_3$, 100 MHz) δ 139.4, 137.2, 131.9, 130.8, 120.3, 116.7, 40.0; Anal HRMS Calcd. for C$_9$H$_9$Br (M): 195.9888. Found: 195.9887.

EXAMPLE 19

4-Allylbenzonitrile

To a solution of t-butylnitrite (535 µl, 4.5 mmol) and allyl bromide (3.9 ml, 45.0 mmol) in CH$_3$CN (3 ml), 4-aminobenzonitrile (354 mg, 3.0 mmol) was added during 20 minutes, while maintaining the temperature of the reaction mixture at 42–44° C. At the end of the addition of the aniline, extra t-butylnitrite (180 µl, 1.5 mmol) was added to the reaction mixture which then was stirred at 50° C. for three hours during which extra t-butylnitrite (180 µl, 1.5 mmol) was added. The volatile material in the reaction mixture was removed at reduced pressure. Heptane-ethyl acetate (10 ml, 1:1) was then added to the crude product and the mixture was filtered. Column chromatography (heptane-ethyl acetate 49:1) of the concentrated filtrate gave 160 mg (37%) 4-allyl-benzonitrile as a clear oil containing 16% of 4-bromo-benzonitrile. This corresponds to 30% yield of 4-allylbenzonitrile. $^1$H NMR (CDCl$_3$, 400 MHz) δ 7.60, (m, 2H, J=8.3 Hz), 7.31, (m, 2H, J=8.3 Hz), 5.99–5.88, (m, 1H), 5.18–5.08, (m, 2H), 3.46, (d, 2H, J=6.7 Hz); Anal HRMS Calcd. for C$_{10}$H$_9$N (M): 143.0735. Found: 143.0734.

EXAMPLE 20

3-Allylnitrobenzene

To a solution of t-butylnitrite (535 µl, 4.5 mmol) and allyl bromide (3.9 ml, 45.0 mmol) in CH$_3$CN (30 ml), 3-nitroaniline (414 mg, 3.0 mmol) was added during 20 minutes, while maintaining the temperature of the reaction mixture at 34–36° C. At the end of the addition of the aniline, extra t-butylnitrite (180 µl, 1.5 mmol) was added to the reaction mixture which then was stirred at 35° C. for one hour. The volatile material in the reaction mixture was removed at reduced pressure. Column chromatography (heptane-ethyl acetate 47:3) gave 420 mg of 3-allylnitrobenzene as a light yellow oil containing 36% of 3-bromonitrobenzene. This corresponds to 50% yield of 3-allylnitrobenzene. $^1$H NMR (CDCl$_3$, 400 MHz) δ 8.10–8.08, (m, 1H), 8.08–8.05, (m, 1H), 7.56–7.51, (m, 1H), 7.50–7.44, (m, 1H), 6.02–5.91, (m, 1H), 5.20–5.10, (m, 2H), 3.50, (d, 2H, J=6.7 Hz); $^{13}$C NMR (CDCl$_3$, 100 MHz) δ 148.8, 142.5, 136.1, 135.3, 129.7, 123.9, 121.8, 117.8, 40.1.

EXAMPLE 21

4-Allylnitrobenzene

To a solution of t-butylnitrite (535 µl, 4.5 mmol) and allyl bromide (3.9 ml, 45.0 mmol) in CH$_3$CN (30 ml), 4-nitroaniline (414 mg, 3.0 mmol) was added during 20 minutes, while maintaining the temperature of the reaction mixture at 34–36° C. At the end of the addition of the aniline, extra t-butylnitrite (180 µl, 1.5 mmol) was added to the reaction mixture which then was stirred at 35° C. for one hour. The volatile material in the reaction mixture was removed at reduced pressure. Column chromatography (heptane-ethyl acetate 23:2) gave 330 mg of 4-allylnitrobenzene as a light yellow oil containing 15% of 4-bromonitrobenzene. This corresponds to 55% yield of 4-allylnitrobenzene. $^1$H NMR (CDCl$_3$, 300 MHz) δ 8.16, (m, 2H, J=8.6 Hz), 7.35, (m, 2H, J 8.6 Hz), 6.02–5.88, (m, 1H), 5.19–5.08, (m, 2H), 3.49, (d, 2H, J=6.6 Hz).

EXAMPLE 22

2-Allyl-5-nitropyridine

To a solution of t-butylnitrite (535 µl, 4.5 mmol) and allyl bromide (3.9 ml, 45.0 mmol) in CH$_3$CN (4 ml), 2-amino-5-nitropyridine (417 mg, 3.0 mmol) was added during 20 minutes, while maintaining the temperature of the reaction mixture at 35–38° C. At the end of the addition of the aniline, extra t-butylnitrite (180 µl, 1.5 mmol) was added to the reaction mixture which then was stirred at 37° C. for one hour. The volatile material in the reaction mixture was removed at reduced pressure to give a crude product containing 2-allyl-5-nitropyridine. $^1$H NMR (CDCl$_3$, 300 MHz) δ 9.37, (d, 1H, J=2.8 Hz), 8.41, (dd, 1H, J=8.6, 2.7 Hz), 7.39, (d, 1H, J=8.4 Hz), 6.12–5.97, (m, 1H), 5.27–5.18, (m, 2H), 3.72, (m, 2H, J=6.8, 1.4 Hz).

EXAMPLE 23

3.5-Dinitro-1-(2-phenyl-2-propenyl)benzene

To a solution of t-butylnitrite (119 µl, 1.0 mmol) and 2-phenyl-3-brompropene (0.99 g, 5.0 mmol) in CH$_3$CN (0.5 ml) was 3,5-dinitroaniline (92 mg, 0.5 mmol) added during 10 minutes, while maintaining the temperature of the reaction mixture at 23–28° C. At the end of the addition of the aniline extra t-butylnitrite (119 µl, 1.0 mmol) was added to the reaction mixture which then was heated to 35° C. for 5 minutes. The reaction mixture was stirred at 22° C. for one hour. The volatile material in the reaction mixture was removed at reduced pressure. Column chromatography (heptane-ethyl acetate 23:2) succeeded by crystallization from heptane gave 50 mg (35%) of 3,5-dinitro-1-(2-phenyl-2-propenyl)benzene as bright yellow needles. $^1$H NMR (CDCl$_3$, 400 MHz) δ 8.88, (t, 1H, J=2.1 Hz), 8.42, (d, 2H, J=2.1 Hz), 7.42–7.37, (m, 2H), 7.36–7.24, (m, 3H), 5.65, (s, 1H), 5.22, (d, 1H, J=0.8 Hz), 4.08, (s, 2H).

EXAMPLE 24

3,5-Dinitro-1-(2-bromo-2-propenyl)benzene

To a solution of t-butylnitrite (535 µl, 4.5 mmol) and allyl bromide (3.9 ml, 45.0 mmol) in CH$_3$CN (3 ml), 3,5-dinitroaniline (549 mg, 3.0 mmol) was added during 20 minutes, while maintaining the temperature of the reaction mixture at 11–15° C. At the end of the addition of the aniline extra t-butylnitrite (180 µl, 1.5 mmol) was added to the reaction mixture which then was stirred at 22° C. for one hour. The volatile material in the reaction mixture was removed at reduced pressure. Column chromatography (heptane-ethyl acetate 10:1) gave 800 mg (93%) 3,5-dinitro-1-(2-bromo-2-propenyl)benzene as a yellow oil. $^1$H NMR (CDCl$_3$, 400 MHz) δ 8.98, (t, 1H, J=2.1 Hz), 8.47, (d, 2H, J=2.1 Hz), 5.89, (m, 1H), 5.71, (d, 1H, J=2.1 Hz), 4.00, (s, 2H); $^{13}$C NMR (CDCl$_3$, 100 MHz) δ 149.05, 142.1, 129.6, 129.3, 121.4, 118.2, 47.3.

EXAMPLE 25

3-(3.5-Dinitrophenyl)cyclohexene

To a solution of t-butylnitrite (119 µl, 1.0 mmol) and 3-bromocyclohexene (860 µl, 7.5 mmol) in CH$_3$CN (0.5 ml), 3,5-dinitroaniline (92 mg, 0.5 mmol) was added during 10 minutes, while maintaining the temperature of the reaction mixture at 23–30° C. After stirring for one hour at room temperature the volatile material in the reaction mixture was removed at reduced pressure. Column chromatography (heptane-ethyl acetate 23:2) followed by preparative HPLC gave 15 mg (12%) of 3-(3,5-dinitrophenyl)cyclohexene as bright yellow crystals. $^1$H NMR (CDCl$_3$, 300 MHz) δ 8.90, (t, 1H, J=2.1 Hz), 8.42, (d, 2H, J=2.1 Hz), 6.19–6.06, (m, 1H), 5.74–5.66, (m, 1H), 3.67, (m, 1H), 2.25–2.07, (m, 3H), 1.80–1.51, (m, 3H).

EXAMPLE 26

2-(3,5-Dinitrobenzyl)acrylic acid

To a solution of t-butylnitrite (535 μl, 4.5 mmol) and 2-(bromomethyl)acrylic acid (7.42 g, 45.0 mmol) in CH$_3$CN (10 ml), 3,5-dinitroaniline (549 mg, 3.0 mmol) was added during 20 minutes, while maintaining the temperature of the reaction mixture at 15–20° C. At the end of the addition of the aniline extra t-butylnitrite (180 μl, 1.5 mmol) was added to the reaction mixture. After heating to 35° C. for 5 minutes, the mixture was stirred at room temperature for one hour. The volatile material in the reaction mixture was then removed at reduced pressure. The remaining crystalline residue was washed with heptane (5×50 ml) to remove unreacted 2-(bromomethyl)acrylic acid. Column chromatography (heptane-ethyl acetate-methanol-acetic acid 5:4:1:0.04) of the remaining crude product followed by crystallization from toluene gave 450 mg (60%) of 2-(3,5-dinitrobenzyl)acrylic acid as yellow needles. $^1$H NMR (CDCl$_3$, 300 MHz) δ 8.93, (t, 1H, J=2.1 Hz), 8.43, (d, 2H, J=2.1 Hz), 6.56, (s, 1H), 5.93, (m, 1H), 3.85, (s, 2H).

Many of the allylic aromatic compounds produced by the process of the invention, in particular the products of Examples 1–4, 7–13, 15, 17 and 22–26 above, are new compounds and are a further feature of the invention.

One group of these new compounds can be represented by general formula (3):

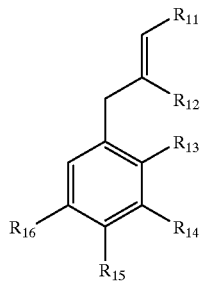

in which:

$R_{11}$ is H or —COOH, $R_{12}$ is H or Br or a phenyl, methyl or —CH$_2$OCOCH$_3$ group, $R_{13}$ is H, Br or Cl or a methyl, —CF$_3$, CN or benzoyl group $R_{14}$ and $R_{16}$ are, independently, H or Br or a NO$_2$, —CF$_3$, —COOC$_2$H$_5$ or —COCH$_3$ group, and $R_{14}$ is H or a NO$_2$ group, and two of $R_{13}$–$R_{16}$ are H and two are other than H.

$R_{11}$ in these compounds is usually H and $R_{12}$ is preferably H, or Br or phenyl. $R_{13}$ is preferably H, Br, Cl, methyl or —CF$_3$, $R_{15}$ is preferably H or NO$_2$ and $R_{14}$ and $R_{16}$ are H, Br, NO$_2$, —CF$_3$ or —COOC$_2$H$_5$.

Examples of groups of these compounds are those in which $R_{13}$ and $R_{15}$ are H and $R_{14}$ and $R_{16}$ are other than H, and those in which $R_{14}$ and $R_{16}$ are H and $R_{13}$ and $R_{15}$ are other than H. Preferred compounds of these types are those in which at least one, and preferably both, of $R_{14}$ and $R_{16}$ is NO$_2$ ($R_{13}$ and $R_{15}$ being H), and those in which at least one of $R_{13}$ and $R_{15}$ is NO$_2$ ($R_{14}$ and $R_{16}$ being H).

As indicated above, these compounds are useful as intermediates in the preparation of corresponding 2,3-dihydroxypropyl compounds.

What is claimed is:

1. A process for the preparation of an allylic aromatic compound in which an aromatic amine is reacted first with a nitrite and then with an allylic olefin having an eliminatable terminal substituent without the use of metal reagents or catalysts.

2. A process according to claim 1 in which the nitrite is t-butylnitrite.

3. A process according to claim 1 in which the aromatic amine has a phenyl or heterocyclic aromatic group substituted by one or two electron withdrawing groups.

4. A process according to claim 1 in which the aromatic amine is aniline substituted by one or two —NO$_2$, —COOH, —COOCH$_3$, —COOC$_2$H$_5$, —CONH$_2$, —CONHPh, —COCH$_3$, —CN or —CF$_3$ groups.

5. A process according to claim 1 in which the allylic olefin has the formula R$^a$L where R$^a$ is an optionally substituted 2,3-alkenyl group and L is an eliminatable substituent.

6. A process according to claim 1 in which the allylic olefin is allyl bromide.

* * * * *